(12) United States Patent
Allen et al.

(10) Patent No.: US 6,278,042 B1
(45) Date of Patent: Aug. 21, 2001

(54) PLANT ARSENIC TRANSPORTERS

(75) Inventors: Stephen M. Allen; J. Antoni Rafalski; Hajime Sakai, all of Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/461,474

(22) Filed: Dec. 14, 1999

Related U.S. Application Data

(60) Provisional application No. 60/112,562, filed on Dec. 16, 1998.

(51) Int. Cl.[7] .............................. A01H 11/00; A01H 1/00; C12P 21/06; C07K 14/00
(52) U.S. Cl. ..................... 800/295; 800/260; 435/69.1; 435/320.2; 435/252.2; 435/325; 530/350
(58) Field of Search ........................ 530/350; 435/69.1, 435/325, 252.3, 320.1; 800/295, 260

(56) References Cited

PUBLICATIONS

Chen, C.M. et al., (1986) J. Biol. Chem., 261:15030–15038.
Kurdi–Haidar, B. et al., (1996) Genomics 36:486–491.
Palmiter, R.D. et al., (1996) EMBO J. 15:1784–1791.
NCBI General Identifier No. 4757796.
NCBI General Identifier No. 267453.
Nature 356(6364):37–41 (1992).
NCBI General Identifier No. 3510254.
Nature 402(6763):761–768 (1999).

*Primary Examiner*—Karen Cochrane Carlson
(74) *Attorney, Agent, or Firm*—Kening Li

(57) ABSTRACT

This invention relates to an isolated nucleic acid fragment encoding a heavy metal transporter. The invention also relates to the construction of a chimeric gene encoding all or a portion of the heavy metal transporter, in sense or antisense orientation, wherein expression of the chimeric gene results in production of altered levels of the heavy metal transporter in a transformed host cell.

24 Claims, 4 Drawing Sheets

Arsenite Transporter Alignment

```
Human      ----------MLL-------------------------------------DVEPLEPTLSNIIEQ
Corn       ARAAGASAIAVRLL----STLRQIPSLSPTRGYRSRSMASAVVVDAGDAPEPTVRNLLDQ
Soybean    M-----------------------------------------------GDQVEGTVQNVLEQ
Wheat      PTANSPVQGNGSLLLFSRHQLRQ-RTLQPHRTFRPK--MSTAVISAEDALEPSLQSLLDQ
Nematode   ----------M-----------------------------------------SDQLEASIKNILEQ Human      RSLKWIFVGGKGGVGKTTCSCSLAVQLSKGRESVLIISTDPAHNISDAFDQKFSKVPTKV
Corn       ESLKWFVGGKGGVGKTTCSSILSVLLAGVRSSVLVISTDPAHNLSDAFQQRFTKFPTLV
Soybean    ETLKWFVGGKGGVGKTTCSSILSILLATVRSSVLIISTDPAHNLSDAFQQRFTKTPTLV
Wheat      RSLRWIFVGGKGGVGKTTTSCSLAIQLAKVRRSVLLISTDPAHNLSDAFSQKFGKEARLV
Nematode   KTLKWIFVGGKGGVGKTTCSCSLAAQLSKVRERVLLISTDPAHNISDAFSQKFTKTPTLV Human      KGYDNLFAMEIDPSLGVADVP----DEFFEEDNM--------LSMGKKMMQEAMSAFPGID
Corn       RGFTNLYAMEIDPKVENDDLSN-EGME--------------GFLSELTNAIPGVD
Soybean    NGFSNLYAMEVDPTVEHEDMGGADGMD----------------TLFSELAGAIPGID
Wheat      NGFDNLSAMEIDPNGSIQDMLAGQGEA--DDVNAAAGGPLG-----GMMQDLAFAIPGID
Nematode   EGFKNLFAMEIDSNPNGEGVEMGNIEEMLQNAAQNEGGSGGFSMGKDFLQSFAGGLPGID Human      EAMSYAEVMRLVKGMNFSVVVFDTAPTGHTLRLLNFPTIVERGLGRLMQIKNQISPFISQ
Corn       EAMSFAEMLKLVQTMDYSVVVFDTAPTGHTLRLLQFPATLEKGLEKMMELKNRFGGLLNQ
Soybean    EAMSFAEMLKLVQTMDYSVIVFDTAPTGHTLRLLQFPSVLEKGLAKVMSLKNKFGGLFNQ
```

FIG. 1A

```
Wheat      EAMSFAEVLKQVKSLSYETIVFDTAPTGHTLRFLQFPTVLEKALAKVSQLSSQYGPLLNG
Nematode   EAMSFGEMIKLIDSLDFDVVVFDTAPTGHTLRLLQFPTLLEKVFTKILSLQGMFGPMMNQ Human      MCNMLGL---GDMNADQLASKLEETLPVIRSVSEQFKDPEQTTFICVCIAEFLSLYETERL
Corn       ASRLFG-LGDELNEDAMLGKLEGMKDVIEQVNRQFKDPDLTTFVCVCIPEFLSLYETERL
Soybean    MTRMFG-MGDDFGDDQILGRLEGMKDVIEQVNKQFKDPDMTTFVCVCIPEFLSLYETERL
Wheat      FLGSGQLPNGQNLNDMIQKLESLRETIGEVNTQFQDAELTTFVCVCIAEFLSLYETERM
Nematode   FGGMFGM--GGGSMNEMIEKMTTTLESVKKMNAQFKDPNCTTFVCVCIAEFLSLYETERL Human      IQELAKCKIDTHNIIVNQLVFPDPEK----PCKMCEARHKIQAKYLDQMEDLY-EDFHIV
Corn       VQELAKFEIDSHNIIINQVIFDEEAVESKLL-----KARMKMQQKYIDQFHMLY-DDFNIT
Soybean    VQELTKFEIDTHNIIINQVIFDDEDVESKLL-----KARMKMQQKYLDQFYMLY-DDFNIT
Wheat      IQELAGYGIDTHSIVVNQLLFPKKASD-----CDQCNARRKMQRKYLDQYELYAEDFNVV
Nematode   IQELSKQGIDTHNIIVNQLLFPDTDANGTVSCRKCASRQAIQSKYLTDIDELY-EDFHVV Human      KLPLLPHEVRGADKVNTFSALLLEPYKPPSAQ----------------------------
Corn       KLPLLSEEVCGVQALQNFSQHFLTPYKSTLKRGT-VEELEQRITILKSALQEAETELDRV
Soybean    KLPLLPEEVTGIEALKAFSRHFTSPYQGLCGKGDPVERLERKVSALQRQLHEAEELERL
Wheat      KMPLLVEEVRGKEKLEKFSEMLVTPYVPP--E----------------------------
Nematode   KLPLLEAEVRGGPAILQFSERMVDP---EANKN---------------------------

Human      --------
Corn       RKGKQSV
Soybean    KRG-----
Wheat      --------
Nematode   --------
```

FIG. 1B

Zinc Transporter (ZnT-2) Alignment

```
Corn         HELLFRPGSRELGSESWVGLELEN-RLRRSTQKDS------------------------MESH
Rice         HELTCKLVPNSARAYTRSLLPISNARTRHHHHLDAGGDHGDNGGGREALLIPKMDSH
Soybean      --------------------------------------------------------EGTS
Wheat        ----------------------------------------------------------
Arabidopsis  --------------------------------------------------------MESS Corn         NPSHSQIAEVTMDIAASASGAAGSKFCKGAACDFSDASNSSKDARERSASMRKLIVAVVL
Rice         NSAPPQIAEVRMDISSSTSVAAGNKVCRGAACDFSDSSNSSKDARERMASMRKLIIAVIL
Soybean      ------------------------------------------------------------
Wheat        ------------------------------------------------------------
Arabidopsis  SPHHSHIVEVNVGKSDEERIIVASKVCGEAPCGFSDSKNASGDAHERSASMRKLCIAVVL Corn         CVVEMAVEVVGGIKANSLAILTDAAHLLSDVAAFAISLFSLWAAGWEATPRQSYGFFRVE
Rice         CIIFMAVEVVGGIKANSLAILTDAAHLLSDVAAFAISLFSLWAAGWEATPQQSYGFFRIE
Soybean      ----MTVEVVGGIKANSLAILTDAAHLLSDVASFAISLFSLWAAGWEATPRQSYGFFRIE
Wheat        ------------------------------------------------------------
Arabidopsis  CLVFMSVEVVGGIKANSLAILTDAAHLLSDVAAFAISLFSLWAAGWEATPRQTYGFFRIE Corn         ILGALVSIQLIWLLAGILVYEAVVRLVGESGDVRGSLMFAVSAFGLAVNVLMAVLLGHDH
Rice         ILGALVSIQLIWLLAGILVYEAIVRLINESGEVQGSLMFAVSAFGLFVNIIMAVLLGHDH
Soybean      ILGALVSIQMIWLLAGILVYEAIDRIIAGPKNVDGFLMFLVSAFGLVVNIIMALLLGHDH
Wheat        ------------------------------------------------------------
Arabidopsis  ILGALVSIQLIWLLTGILVYEAIIRIVTETSEVNGFLMFLVAAFGLVVNIIMAVLLGHDH
```

FIG. 2A

```
Corn         GHGH-GHGHGHSHD-HGHGHGDSDDGHSHHDDEEQEQGRVHHHEHGHGGAITVTTHHHHH
Rice         GHGH-GHGHGHGHS-HDHDHGGSD---HDHHHHEDQEHGHVHHHEDGHGNSITVNLHHHPG
Soybean      GHRHAGHSHGHGHDGHGHSHGFTMSTHCDAKHTKDQHHHTHHHDENHPKDAHHHTDEDHL
Wheat        ------------------------------------------------------------
Arabidopsis  GHSH-GHGHGHGHDHHNHSHGVTVTTH------HHHHDHEHGHSHGHGEDKH--------

Corn         ---HHDHDVEEALIKHEG----TQSAGRAGKKPRRNINVHSAYLHVLGDSVQSVGVMVGGA
Rice         TGHHHHDAEEPLLKSDAGCDSTQSGAKDAKKARRNINVHSAYLHVLGDSIQSIGVMIGGA
Soybean      HHHAHKEVTELLL----GESKG--GTKKKKQWNINVQGAYLHVLGDSIQSIGVMIGGA
Wheat        ---------------------TRSGAKPAKKPRRNINVHSAYLHVIGDSIQSIGVMIGGA
Arabidopsis  ---HAHGDVTEQLL-------DKSKTQVAAKEKRKRNINLQGAYLHVLGDSVGVMIGGA Corn         IIWYKPEWKVIDLICTLVFSVVVLFTTIRMLRSILEVLMESTPREIDATRLESGLCGMEG
Rice         IIWYKPEWKIIDLICTLIFSVIVLFTTIKMLRNILEVLMESTPREIDATSLENGLRDMDG
Soybean      VIWYNPRWQIVDLICTLIFSVIVMGTTINMLRNILEVLMENTPREIDATKLERGLLDMED
Wheat        LIWYKPEWKIIDLICTLIFSVIVLFTTIRMIRNILEVLMESTPREIDATRLESGLREMEG
Arabidopsis  IIWYNPEWKVIDLICTLAFSVIVLGTTINMIRNILEVLMESTPREIDATKLEKGLLEMEE Corn         VVAVHELHIWAITVGKVLLACHVTIARDADADEILDKVIGYIKTEYNISHVTIQVERE
Rice         VVAVHELHIWAITVGKVLLACHVTIACHVTITQDADADQMLDKVIGYIKSEYNISHVTIQIERE
Soybean      VVAVHELHIWAITVGKVLLACHVKIRREADADLVLDKVIDYIKRVYNISHVTIQIER-
Wheat        VIAVHELHIWAITVGKVLLACHVTITQDADADKMLDKVIGYIKAEYNISHVTIQIERE
Arabidopsis  VVAVHELHIWAITVGKVLLACHVNIRPEADADMVLNKVIDYIRREYNISHVTIQIER-
```

FIG. 2B

PLANT ARSENIC TRANSPORTERS

This application claims the benefit of U.S. Provisional Application No. 60/112,562, filed Dec. 16, 1998.

FIELD OF THE INVENTION

This invention is in the field of plant molecular biology. More specifically, this invention pertains to nucleic acid fragments encoding heavy metal transporters in plants and seeds.

BACKGROUND OF THE INVENTION

Arsenite extrusion pumps have been identified in bacteria, mice and humans. A hydrophilic transporter belonging to the ATPase superfamily, having no transmembrane domain and having two potential adenylate-binding sites has been studied in arsenite-resistant bacteria (Chen, C. M. et al. (1986) *J. Biol. Chem.* 261:15030–15038). Lower molecular weight homologs have been found in mice and humans where the different domains may be encoded by two different genes (Kurdi-Haidar, B. et al. (1996) *Genomics* 36:486–491).

Plants require certain essential elements for completing their life cycle. Energy from sunlight and availability of the essential elements allows plants to synthesize the compounds necessary for their normal growth. One of these essential elements is zinc which is absorbed from the soil, is required for the activity of many enzymes and is required for chloroplast biosynthesis in some plants. Zinc deficiency results in small plants with distorted leaves; in some species such as corn, sorghum and beans the leaves show necrotic spots and chlorosis. Excess zinc is also detrimental for plants. To prevent zinc toxic buildup in the cytosol, plants may sequester it in the vacuole. The zinc transporter ZnT-2 protects cells from zinc toxicity by facilitating vacuolar zinc transport into an endosomal/lysosomal compartment (Palmiter, R. D. et al. (1996) *EMBO J*. 15:1784–1791).

SUMMARY OF THE INVENTION

The present invention relates to isolated polynucleotides comprising a nucleotide sequence encoding a polypeptide of at least 60 amino acids that has at least 55% identity based on the Clustal method of alignment when compared to a polypeptide selected from the group consisting of a corn arsenite transporter polypeptide of SEQ ID NO:2, a soybean arsenite transporter polypeptide of SEQ ID NO:4, and a wheat arsenite transporter polypeptide of SEQ ID NO:6, and isolated polynucleotides comprising a nucleotide sequence encoding a polypeptide of at least 157 amino acids that has at least 80% identity based on the Clustal method of alignment when compared to a polypeptide selected from the group consisting of a corn zinc transporter polypeptide of SEQ ID NO:8, a rice zinc transporter polypeptide of SEQ ID NO:10, a soybean zinc transporter polypeptide of SEQ ID NO:12, and a wheat zinc transporter polypeptide of SEQ ID NO:14. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, 5, 7, 9, 11, and 13 that codes for the polypeptide selected from the group consisting of SEQ ID NOs:2, 4, 6, 8, 10, 12, and 14. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, 11, and 13, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to an arsenite transporter polypeptide of at least 60 amino acids comprising at least 55% homology based on the Clustal method of alignment compared to a polypeptide selected from the group consisting of SEQ ID NOs:2, 4, and 6, and a zinc transporter polypeptide of at least 157 amino acids comprising at least 80% homology based on the Clustal method of alignment compared to a polypeptide selected from the group consisting of SEQ ID NOs:8, 10, 12, and 14.

The present invention relates to a method of selecting an isolated polynucleotide that affects the level of expression of an arsenite or zinc transporter polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level an arsenite or zinc transporter polypeptide in the host cell containing the isolated polynucleotide; and (d) comparing the level of an arsenite or zinc transporter polypeptide in the host cell containing the isolated polynucleotide with the level of an arsenite or zinc transporter polypeptide in the host cell that does not contain the isolated polynucleotide.

The present invention relates to a method of obtaining a nucleic acid fragment encoding a substantial portion of an arsenite or zinc transporter polypeptide gene, preferably a plant arsenite or zinc transporter polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, and 13, and the complement of such nucleotide sequences; and amplifying a nucleic acid fragment (preferably a cDNA inserted in a cloning vector) using the oligonucleotide primer. The amplified nucleic acid fragment preferably will encode a portion of an arsenite or zinc transporter amino acid sequence.

The present invention also relates to a method of obtaining a nucleic acid fragment encoding all or a substantial portion of the amino acid sequence encoding an arsenite or zinc transporter polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Heavy Metal Transporters

| | | | SEQ ID NO: | |
| --- | --- | --- | --- | --- |
| Protein | Plant Species | Clone Designation | Nucleotide | Amino Acid |
| Arsenite transporter | Maize [Zea mays] | cen1.pk0113.d6:fis | 1 | 2 |
| | Soybean [Glycine max] | sgs2c.pk002.e14:fis | 3 | 4 |
| | Wheat [Triticum aestivum] | w11n.pk0142.e2:fis | 5 | 6 |
| Zinc transporter (ZnT-2) | Maize [Zea mays] | cdt2c.pk002.h12:fis | 7 | 8 |
| | Rice [Oryza sativa] | r10n.pk0012.c11:fis | 9 | 10 |
| | Soybean [Glycine max] | se6.pk0012.h2:fis | 11 | 12 |
| | Wheat [Triticum aestivum] | wlm4.pk0016.h1:fis | 13 | 14 |

The present invention relates to a composition, such as a hybridization mixture, comprising an isolated polynucleotide of the present invention.

The present invention relates to an isolated polynucleotide of the present invention comprising at least one of 30 contiguous nucleotides derived from a nucleic acid sequence selected from the group consisting of SEQ ID NOs:1, 3, 5, 7, 9, 11, and 13.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the arsenite or zinc transporters polynucleotide in an amount sufficient to complement a sensitivity to high levels of heavy metals to provide a positive selection means.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 shows a comparison of the amino acid sequences of the arsenite transporter polypeptides from corn [Zea mays], soybean [Glycine max], and wheat [Triticum aestivum] (SEQ ID NOs:2, 4, and 6, respectively) to the arsenite transporter polypeptides from human [Homo sapien]and nematodes [Caenorhabditis elegans] (SEQ ID NOs:15 and 16).

FIG. 2 shows a comparison of the amino acid sequences of the zinc transporter (ZnT-2) polypeptides from corn [Zea mays], rice [Oryza sativa], soybean [Glycine max], and wheat [Triticum aestivum] (SEQ ID NOs:8, 10, 12, and 14, respectively) to the zinc transporter polypeptide from Arabidopsis thaliana] (SEQ ID NO:17).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing.

The Sequence Listing contains the one letter code for nucleotide sequence characters and the three letter codes for amino acids as defined in conformity with the IUPAC-IUBMB standards described in Nucleic Acids Res. 13:3021–3030 (1985) and in the Biochemical J. 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, and 13, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, and 13, and the complement of such nucleotide sequences may be used in methods of selecting an isolated polynucleotide that affects the expression of a polypeptide (such as an arsenite or zinc transporter) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol.*

Biol. 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or finctional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several heavy metal transporters have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other arsenite or zinc transporters, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, and 13, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as arsenite or zinc transporters) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, and 13, and the complement of such nucleotide sequences; and amplfying a nucleic acid fragment (preferably a cDNA inserted in a cloning vector) using the oligonucleotide primer. The amplified nucleic acid fragment preferably will encode a portion of a polypeptide of arsenite or zinc transporter.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of of heavy metal tolerance in those cells. Growing plants overexpressing any one of these transporters may help cleanup of polluted grounds.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded heavy metal transporters. An example of a vector for high level expression of the instant polypeptides in a bacterial host is provided (Example7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used or physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries, Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
| --- | --- | --- |
| cdt2c | Corn (*Zea mays* L.) developing tassel 2 | cdt2c.pk002.h12:fis |
| cen1 | Corn Endosperm 10 to 11 Days After Pollination | cen1.pk0113.d6:fis |
| r10n | Rice 15 Day Old Leaf* | r10n.pk0012.c11:fis |
| se6 | Soybean Embryo, 26 Days After Flowering | se6.pk0012.h2:fis |
| sgs2c | Soybean Seeds 14 Hours After Germination | sgs2c.pk002.e14:fis |
| w11n | Wheat Leaf From 7 Day Old Seedling* | w11n.pk0142.e2:fis |
| wlm4 | Wheat Seedlings 4 Hours After Inoculation With *Erysiphe graminis* f. sp tritici | wlm4.pk0016.h1:fis |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding heavy metal transporters were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Arsenite Transporter

The BLASTX search using the EST sequences from clones listed in Table 3 revealed similarity of the polypeptides encoded by the cDNAs to arsenite transporter from human (*Homo sapiens*) or nematode (*Caenorhabditis elegans*) (NCBI Accession No. gi 4757796 or gi 267453, respectively). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to Arsenite Transporter

| Clone | Status | BLAST pLog Score |
| --- | --- | --- |
| | | 4757796 |
| cen1.pk0113.d6:fis | FIS | 98.00 |
| sgs2c.pk002.e14:fis | FIS | 98.50 |
| | | BLAST pLog Score |
| | | 267453 |
| w11n.pk0142.e2:fis | FIS | 97.70 |

FIG. 1 presents an alignment of the amino acid sequences set forth in SEQ ID NOs:2, 4 and 6, and the human and nematode sequences (SEQ ID NOs:15 and 16, respectively). The data in Table 4 represents a calculation of the percent identity of the amino acid sequences set forth in SEQ ID NOs:2, 4 and 6, and the human and nematode sequences (SEQ ID NOs:15 and 16, respectively).

TABLE 4

Percent Identity of Amino Acid Sequences Deduced From the Nucleotide Sequences of cDNA Clones Encoding Polypeptides Homologous to Arsenite Transporter

| SEQ ID NO. | Percent Identity to 4757796 |
|---|---|
| 2 | 51.5% |
| 4 | 50.9% |
| | Percent Identity to 267453 |
| 6 | 50.9% |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an arsenite transporter. These sequences represent the first plant sequences encoding arsenite transporter.

Example 4

Characterization of cDNA Clones Encoding Zinc Transporter (ZnT-2)

The BLASTX search using the EST sequences from clones listed in Table 3 revealed similarity of the polypeptides encoded by the cDNAs to zinc transporter (ZnT-2) from *Arabidopsis thaliana* (NCBI Accession No. gi 3510254). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Resultstor Sequences Encoding Polypeptides Homologous to Zinc Transporter (ZnT-2)

| Clone | Status | BLAST pLog Score 3510254 |
|---|---|---|
| cdt2c.pk002.h12:fis | FIS | 160.00 |
| r10n.pk0012.c11:fis | FIS | 161.00 |
| se6.pk0012.h2:fis | FIS | 149.00 |
| wlm4.pk0016.h1:fis | FIS | 63.70 |

FIG. 2 presents an alignment of the amino acid sequences set forth in SEQ ID NOs:8, 10, 12, and 14, and the *Arabidopsis thaliana* sequence (SEQ ID NO:17). The data in Table 6 represents a calculation of the percent identity of the amino acid sequences set forth in SEQ ID NOs:8, 10, 12, and 14, and the Arabidopsis thaliana sequence (SEQ ID NO:17).

TABLE 5

Percent Identity of Amino Acid Sequences Deduced From the Nucleotide Sequences of cDNA Clones Encoding Polypeptides Homologous to Zinc Transporter (ZnT-2)

| SEQ ID NO. | Percent Identity to 3510254 |
|---|---|
| 8 | 68.8% |
| 10 | 69.6% |
| 12 | 72.5% |
| 14 | 75.8% |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a zinc transporter (ZnT-2). These sequences represent the first monocot (corn, rice, wheat) and soybean sequences encoding zinc transporter (ZnT-2).

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6
Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7
Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuiged and the protein concentration of the supernatant determined. One µg of protein from the soluble fraction of the culture can be separated by SDS-polyacrylamide gel electrophoresis. Gels can be observed for protein bands migrating at the expected molecular weight.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated arsenic transporter that has a sequence identity of at least 55% based on the Clustal method compared to an amino acid sequence selected from the group consisting of SEQ ID NOs: 2, 4, and 6.

2. The isolated polypeptide of claim 1 wherein the sequence identity is at least 70%.

3. The isolated polypeptide of claim 1 wherein the sequence identity is at least 80%.

4. The isolated polypeptide of claim 1 wherein the sequence identity is at least 85%.

5. The isolated polypeptide of claim 1 wherein the sequence identity is at least 90%.

6. The isolated polypeptide of claim 1 wherein the sequence identity is at least 95%.

7. The polypeptide of claim 1 wherein the polypeptide has a sequence selected from the group consisting of SEQ ID NOs:2, 4, and 6.

8. An isolated polynucleotide that encodes a an arsenic transporter polypeptide, the polypeptide having a sequence identity of at least 55% based on the Clustal method of alignment when compared to a polypeptide selected from the group consisting of SEQ ID NOs:2, 4, and 6.

9. The polynucleotide of claim 24 wherein the sequence identity is at least 70%.

10. The polynucleotide of claim 8 wherein the sequence identity is at least 80%.

11. The polynucleotide of claim 8 wherein the sequence identity is at least 85%.

12. The polymucleotide of claim 8 wherein the sequence identity is at least 90%.

13. The polynucleotide of claim 8 wherein the sequence identity is at least 95%.

14. The polynucleotide of claim 8 wherein the polynucleotide encodes a polypeptide selected from the group consisting of SEQ ID NOs:2, 4, and 6.

15. The polynucleotide of claim 8, wherein the polynucleotide comprises a nucleotide sequence selected from the group consisting of SEQ ID NO:1, 3, and 5.

16. An isolated complement of the polynucleotide of claim 8, wherein (a) the complement and the polynucleotide consist of the same number of nucleotides, and (b) the nucleotide sequences of the complement and the polynucleotide have 100% complementarity.

17. An isolated polynucleotide that (1) comprises at least 180 contiguous nucleotides and (2) remains hybridized with the isolated polynucleotide of claim 8 under a wash condition of 0.1×SSC, 0.1% SDS, and 65° C.

18. A chimeric gene comprising the polynucleotide of claim 8 operably linked to at least one regulatory sequence.

19. A virus comprising the polynucleotide of claim 8.

20. A method for transforming a cell comprising introducing into a cell the polynucleotide of claim 8.

21. A cell comprising the polynucleotide of claim 8.

22. The cell of claim 21, wherein the cell is selected from the group consisting of a yeast cell, a bacterial cell and a plant cell.

23. A method for producing a transgenic plant comprising (a) transforming a plant cell with the polynucleotide of claim 8, and (b) regenerating a plant from the transformed plant cell.

24. A transgenic plant produced by the method of claim 39.

* * * * *

UNITED STATES PATENT AND TRADEMARK OFFICE
CERTIFICATE OF CORRECTION

PATENT NO. : 6,278,042 B1
DATED : August 21, 2001
INVENTOR(S) : Allen Stephen M., Rafalski J Antoni and Sakai Hajime It is certified that error appears in the above-identified patent and that said Letters Patent is hereby corrected as shown below:

Column 52,
Line 65, change "39" to -- 23 --.

Signed and Sealed this

Twenty-seventh Day of April, 2004

JON W. DUDAS
*Acting Director of the United States Patent and Trademark Office*

SEQUENCE LISTING

<160> NUMBER OF SEQ ID NOS: 17

<210> SEQ ID NO 1
<211> LENGTH: 1387
<212> TYPE: DNA
<213> ORGANISM: Zea mays

<400> SEQUENCE: 1
gcacgagcag caggtgccag cgccatcgcc gttcgcctcc tctccacact ccgccagatc     60
ccatccctct cgcccacgcg cgggtatcgg agtcggagca tggcgtctgc agtggtggtg    120

-continued

```
gacgccggcg acgcgccgga gcccacggtt cgtaacctcc tggaccagga gtccctcaag     180
tgggtcttcg tcggcgggaa gggcggcgtc ggcaagacta cctgcagctc catcctctcc     240
gtcctcctcg ccggggtccg ctcgtccgtg ctcgtcatct ccaccgaccc cgcgcacaac     300
ctcagcgacg ccttccagca gcgcttcacc aagttcccca ctctcgtccg cggattcacc     360
aacctctacg ccatggaaat tgacccaaag gtagaaaatg atgatttatc caatgaagga     420
atggaaggat tcctgtcaga actgacaaat gcgattccag gagtagatga agctatgagt     480
tttgctgaaa tgctaaaatt agtccaaaca atggattact ctgttgtagt ttttgatact     540
gctcctacag ggcatacatt acggttgctt cagttcccag caaccctaga agggtctt      600 gagaaaatga tggagttgaa aaatagattt ggcggtctgt tgaatcaggc cagtcgattg     660
tttggtcttg gtgatgagct gaacgaggat gcaatgcttg ggaaacttga gggtatgaag     720
gatgtgatcg aacaagtgaa caggcaattt aaagatccag acttgacaac ttttgtatgt     780
gtttgtatcc cggaatttct ttcattgtat gaaacagaaa gattggtgca agagttagcg     840
aagtttgaga ttgattcaca caatattatt attaatcaag ttatatttga tgaggaagct     900
gtcgagtcaa aactgctaaa agcacggatg aaaatgcaac aaaaatacat tgatcagttc     960
catatgttat acgatgactt caacatcacc aagcttccct tgctttcaga agaggtttgt    1020
ggtgttcaag ctctccaaaa cttttcccag cacttcctta caccatacaa gtctactctt    1080
aaaaggggca ccgtcgagga gctcgaacag agaataacta tattaaaatc tgcactgcaa    1140
gaagctgaga cagagttaga tagggttagg aaagggaagc agtcagtgtg attttttttc    1200
cacaggtcaa gtgtgtaaaa ccagagagac gatcaatttt ttcgtgtcat tacactcttg    1260
ttgatttcac tatcatgttt cctcatcgag gagtttagac ttgtaatagc tatcggcaga    1320
gaagtgtttg attcacacaa gatatataga tccattcttt ttgccggtta aaaaaaaaa     1380 aaaaaaa                                                              1387
```

<210> SEQ ID NO 2
<211> LENGTH: 396
<212> TYPE: PRT
<213> ORGANISM: Zea mays

<400> SEQUENCE: 2

```
Ala Arg Ala Ala Gly Ala Ser Ala Ile Ala Val Arg Leu Leu Ser Thr
 1               5                  10                  15

Leu Arg Gln Ile Pro Ser Leu Ser Pro Thr Arg Gly Tyr Arg Ser Arg
            20                  25                  30

Ser Met Ala Ser Ala Val Val Val Asp Ala Gly Asp Ala Pro Glu Pro
        35                  40                  45

Thr Val Arg Asn Leu Leu Asp Gln Glu Ser Leu Lys Trp Val Phe Val
    50                  55                  60

Gly Gly Lys Gly Gly Val Gly Lys Thr Thr Cys Ser Ser Ile Leu Ser
65                  70                  75                  80

Val Leu Leu Ala Gly Val Arg Ser Ser Val Leu Val Ile Ser Thr Asp
                85                  90                  95

Pro Ala His Asn Leu Ser Asp Ala Phe Gln Gln Arg Phe Thr Lys Phe
            100                 105                 110

Pro Thr Leu Val Arg Gly Phe Thr Asn Leu Tyr Ala Met Glu Ile Asp
        115                 120                 125

Pro Lys Val Glu Asn Asp Asp Leu Ser Asn Glu Gly Met Glu Gly Phe
    130                 135                 140
```

```
Leu Ser Glu Leu Thr Asn Ala Ile Pro Gly Val Asp Glu Ala Met Ser
145                 150                 155                 160

Phe Ala Glu Met Leu Lys Leu Val Gln Thr Met Asp Tyr Ser Val Val
                165                 170                 175

Val Phe Asp Thr Ala Pro Thr Gly His Thr Leu Arg Leu Leu Gln Phe
            180                 185                 190

Pro Ala Thr Leu Glu Lys Gly Leu Glu Lys Met Met Glu Leu Lys Asn
        195                 200                 205

Arg Phe Gly Gly Leu Leu Asn Gln Ala Ser Arg Leu Phe Gly Leu Gly
    210                 215                 220

Asp Glu Leu Asn Glu Asp Ala Met Leu Gly Lys Leu Glu Gly Met Lys
225                 230                 235                 240

Asp Val Ile Glu Gln Val Asn Arg Gln Phe Lys Asp Pro Asp Leu Thr
                245                 250                 255

Thr Phe Val Cys Val Cys Ile Pro Glu Phe Leu Ser Leu Tyr Glu Thr
            260                 265                 270

Glu Arg Leu Val Gln Glu Leu Ala Lys Phe Glu Ile Asp Ser His Asn
        275                 280                 285

Ile Ile Ile Asn Gln Val Ile Phe Asp Glu Glu Ala Val Glu Ser Lys
    290                 295                 300

Leu Leu Lys Ala Arg Met Lys Met Gln Gln Lys Tyr Ile Asp Gln Phe
305                 310                 315                 320

His Met Leu Tyr Asp Asp Phe Asn Ile Thr Lys Leu Pro Leu Leu Ser
                325                 330                 335

Glu Glu Val Cys Gly Val Gln Ala Leu Gln Asn Phe Ser Gln His Phe
            340                 345                 350

Leu Thr Pro Tyr Lys Ser Thr Leu Lys Arg Gly Thr Val Glu Glu Leu
        355                 360                 365

Glu Gln Arg Ile Thr Ile Leu Lys Ser Ala Leu Gln Glu Ala Glu Thr
    370                 375                 380

Glu Leu Asp Arg Val Arg Lys Gly Lys Gln Ser Val
385                 390                 395

<210> SEQ ID NO 3
<211> LENGTH: 1498
<212> TYPE: DNA
<213> ORGANISM: Glycine max

<400> SEQUENCE: 3
gcacgaggaa ggaagaaacc agcgtcactc atctcatcgt ggttctgcaa agtcttcttt      60
tcttttcggt gaattaataa agggttttg cgtggtgatt gtgttgtgtt gtgctgtgct     120
gtgtatctga atccgcgcaa ttaggttttg tgattaattc attgattaat cagagagaga     180
agggggaata atgggagatc aagtggaggg aacggtgcag aacgttctgg aacaggagac     240
tctgaagtgg gtcttcgttg gtggcaaagg cggcgtcggc aaaacgacat gcagttcaat     300
cctatccatt ctcctcgcca ccgttcgctc tccgtcctc atcatctcca ccgaccccgc     360
ccacaacctc agcgacgcct ccagcagcg tttcaccaaa accccaccc tcgtcaatgg     420
cttctccaat ctctacgcca tggaggtgga tcctactgtt gagcatgaag acatgggcgg     480
cgctgatggg atggacacct tgttctctga gctcgccggc gcgattcccg ggattgacga     540
ggccatgagc tttgctgaga gtgttgaaatt ggttcagaca atggattatt ctgttattgt     600
ctttgatact gctcccactg gccatacact cagactattg caattcccat cggttttaga     660
aaagggcctt gcaaaagtga tgtctttgaa aaataaattt ggtggtttgt ttaatcagat     720
```

-continued

```
gactcgcatg tttggcatgg gtgacgattt tggggatgat caaatccttg ggaggcttga    780
aggcatgaag gatgtaattg aacaagttaa taagcaattc aaagatcctg acatgacaac    840
ctttgtctgt gtgtgcattc ctgaattcct ttctctgtat gaaacagaaa gattggttca    900
ggagcttaca aagtttgaaa ttgacactca caatatcatc atcaatcaag ttatctttga    960
tgatgaagat gttgaatcca agttacttaa agcaaggatg aaaatgcaac agaaatatct   1020
ggaccagttt tacatgttgt atgatgactt taacattacc aagctgccat tgctcccaga   1080
ggaggttact gggattgaag ctctgaaagc attttcaaga cattttacat caccatatca   1140
aggcttatgt ggtaaaggag acccggttga acggttagag cgtaaagtat cagcactaca   1200
gcgccagtta catgaggctg aagaagaact ggagagactc aaaaggggca actaggtttg   1260
atggcctcca ttcatgaata atatgtcatt gtattccttt ttggttcaca ttatttttta   1320
gcttaaattt gataaagcat cttttttctt tgttgggctg ccaacacaag tcattcccta   1380 tatgttttt atttaattat tggcacagcg agctttctta tgtaaccccc aaaaaatatt   1440
gctgaggtta gcctaatttg tttcacgaat attcttttca aaaaaaaaaa aaaaaaa     1498
```

<210> SEQ ID NO 4
<211> LENGTH: 353
<212> TYPE: PRT
<213> ORGANISM: Glycine max

<400> SEQUENCE: 4

```
Met Gly Asp Gln Val Glu Gly Thr Val Gln Asn Val Leu Glu Gln Glu
  1               5                  10                  15

Thr Leu Lys Trp Val Phe Val Gly Gly Lys Gly Val Gly Lys Thr
             20                  25                  30

Thr Cys Ser Ser Ile Leu Ser Ile Leu Leu Ala Thr Val Arg Ser Ser
         35                  40                  45

Val Leu Ile Ile Ser Thr Asp Pro Ala His Asn Leu Ser Asp Ala Phe
     50                  55                  60

Gln Gln Arg Phe Thr Lys Thr Pro Thr Leu Val Asn Gly Phe Ser Asn
 65                  70                  75                  80

Leu Tyr Ala Met Glu Val Asp Pro Thr Val Glu His Glu Asp Met Gly
                 85                  90                  95

Gly Ala Asp Gly Met Asp Thr Leu Phe Ser Glu Leu Ala Gly Ala Ile
            100                 105                 110

Pro Gly Ile Asp Glu Ala Met Ser Phe Ala Glu Met Leu Lys Leu Val
        115                 120                 125

Gln Thr Met Asp Tyr Ser Val Ile Val Phe Asp Thr Ala Pro Thr Gly
    130                 135                 140

His Thr Leu Arg Leu Leu Gln Phe Pro Ser Val Leu Glu Lys Gly Leu
145                 150                 155                 160

Ala Lys Val Met Ser Leu Lys Asn Lys Phe Gly Gly Leu Phe Asn Gln
                165                 170                 175

Met Thr Arg Met Phe Gly Met Gly Asp Asp Phe Gly Asp Gln Ile
            180                 185                 190

Leu Gly Arg Leu Glu Gly Met Lys Asp Val Ile Glu Gln Val Asn Lys
        195                 200                 205

Gln Phe Lys Asp Pro Asp Met Thr Thr Phe Val Cys Val Cys Ile Pro
    210                 215                 220

Glu Phe Leu Ser Leu Tyr Glu Thr Glu Arg Leu Val Gln Glu Leu Thr
225                 230                 235                 240
```

```
Lys Phe Glu Ile Asp Thr His Asn Ile Ile Asn Gln Val Ile Phe
                245                 250                 255
Asp Asp Glu Asp Val Glu Ser Lys Leu Leu Lys Ala Arg Met Lys Met
                260                 265                 270
Gln Gln Lys Tyr Leu Asp Gln Phe Tyr Met Leu Tyr Asp Asp Phe Asn
            275                 280                 285
Ile Thr Lys Leu Pro Leu Leu Pro Glu Glu Val Thr Gly Ile Glu Ala
        290                 295                 300
Leu Lys Ala Phe Ser Arg His Phe Thr Ser Pro Tyr Gln Gly Leu Cys
305                 310                 315                 320
Gly Lys Gly Asp Pro Val Glu Arg Leu Glu Arg Lys Val Ser Ala Leu
                325                 330                 335
Gln Arg Gln Leu His Glu Ala Glu Glu Leu Glu Arg Leu Lys Arg
                340                 345                 350
Gly
```

```
<210> SEQ ID NO 5
<211> LENGTH: 1377
<212> TYPE: DNA
<213> ORGANISM: Triticum aestivum

<400> SEQUENCE: 5
gcacgagcct gattctgctc tactctacta ctctctctgt gctgtagcct accgccaaca      60
gcccagtcca gggaaacggt tccttattgc tttttctcg tcaccaactt aggcaacgta     120
ccctacagcc tcatcgcaca tttcgcccaa aaatgtccac cgcagttatc tccgccgagg     180
atgcccttga gccctctcta cagtctctcc tggaccagcg aagccttcgt tggatctttg     240
tcggcggcaa gggcggtgtc ggcaagacca cgacttcttg ctccctcgcg attcagctcg     300
ccaaggttcg acgctctgtt cttctcatct cgaccgatcc cgcccataac ctttcagatg     360
ctttctctca gaagtttggc aaagaggccc gccttgtcaa cgggtttgac aacctgagtg     420
ccatggagat cgacccgaat ggcagcattc aggatatgct agcaggccag ggcgaggccg     480
atgatgtcaa cgctgcggct ggtggtcctc tgggaggcat gatgcaggat ctggcattcg     540
caatccctgg tatcgacgag gctatgtcct ttgccgaagt cctcaagcaa gtcagtcccc     600
tctcatacga gaccatcgtc ttcgacacag ccccgacagg ccacaccctg cgcttcctcc     660
agtttcccac cgttcttgag aaggctctcg caaaggtttc tcaactgtcg tgcagtatg     720 gtcctctcct caacggcttc cttggctccg gaggtcagct acccaacgga cagaacctca     780
atgatatgat tcagaaactt gaatccttgc gagagaccat cggcgaggtc aatactcagt     840
tccaggacgc tgaactcacc acctttgtct gtgtgtgcat tgcagagttt ctgagtctct     900
acgagacgga gcgtatgatt caggagcttg ctggttatgg tatcgatacc cactccatcg     960
ttgtcaacca gctgctcttc cccaagaagg ctagcgattg cgatcagtgc aacgcccgtc    1020
gcaagatgca gcgcaagtat cttgaccagt atgaagaact atatgctgag acttcaatg    1080 tcgtcaagat gcctctgctt gttgaggagg tacgaggaaa ggagaagctt gagaagttta    1140
gtgaaatgct tgttacacct tatgttcctc ctgagtaggg ctggtatcaa gggctaggca    1200
tagaaggtga ggtggaatat gagagaacgg atataaacag tatcacatat aaaagagcac    1260
gggcggcgcg gagttgtaga ataattgatt aatggcttac gataatacac cctagaatta    1320
agctgcagac acagtcaatc accaaaaaag aaaaaaaaaa aaaaaaaaa aaaaaa         1377
```

-continued

```
<210> SEQ ID NO 6
<211> LENGTH: 376
<212> TYPE: PRT
<213> ORGANISM: Triticum aestivum

<400> SEQUENCE: 6

Pro Thr Ala Asn Ser Pro Val Gln Gly Asn Gly Ser Leu Leu Leu Phe
  1               5                  10                  15

Ser Arg His Gln Leu Arg Gln Arg Thr Leu Gln Pro His Arg Thr Phe
             20                  25                  30

Arg Pro Lys Met Ser Thr Ala Val Ile Ser Ala Glu Asp Ala Leu Glu
         35                  40                  45

Pro Ser Leu Gln Ser Leu Leu Asp Gln Arg Ser Leu Arg Trp Ile Phe
     50                  55                  60

Val Gly Gly Lys Gly Val Gly Lys Thr Thr Thr Ser Cys Ser Leu
 65                  70                  75                  80

Ala Ile Gln Leu Ala Lys Val Arg Arg Ser Val Leu Leu Ile Ser Thr
                 85                  90                  95

Asp Pro Ala His Asn Leu Ser Asp Ala Phe Ser Gln Lys Phe Gly Lys
            100                 105                 110

Glu Ala Arg Leu Val Asn Gly Phe Asp Asn Leu Ser Ala Met Glu Ile
        115                 120                 125

Asp Pro Asn Gly Ser Ile Gln Asp Met Leu Ala Gly Gln Gly Glu Ala
    130                 135                 140

Asp Asp Val Asn Ala Ala Ala Gly Gly Pro Leu Gly Gly Met Met Gln
145                 150                 155                 160

Asp Leu Ala Phe Ala Ile Pro Gly Ile Asp Glu Ala Met Ser Phe Ala
                165                 170                 175

Glu Val Leu Lys Gln Val Lys Ser Leu Ser Tyr Glu Thr Ile Val Phe
            180                 185                 190

Asp Thr Ala Pro Thr Gly His Thr Leu Arg Phe Leu Gln Phe Pro Thr
        195                 200                 205

Val Leu Glu Lys Ala Leu Ala Lys Val Ser Gln Leu Ser Ser Gln Tyr
    210                 215                 220

Gly Pro Leu Leu Asn Gly Phe Leu Gly Ser Gly Gln Leu Pro Asn
225                 230                 235                 240

Gly Gln Asn Leu Asn Asp Met Ile Gln Lys Leu Glu Ser Leu Arg Glu
                245                 250                 255

Thr Ile Gly Glu Val Asn Thr Gln Phe Gln Asp Ala Glu Leu Thr Thr
            260                 265                 270

Phe Val Cys Val Cys Ile Ala Glu Phe Leu Ser Leu Tyr Glu Thr Glu
        275                 280                 285

Arg Met Ile Gln Glu Leu Ala Gly Tyr Gly Ile Asp Thr His Ser Ile
    290                 295                 300

Val Val Asn Gln Leu Leu Phe Pro Lys Lys Ala Ser Asp Cys Asp Gln
305                 310                 315                 320

Cys Asn Ala Arg Arg Lys Met Gln Arg Lys Tyr Leu Asp Gln Tyr Glu
                325                 330                 335

Glu Leu Tyr Ala Glu Asp Phe Asn Val Val Lys Met Pro Leu Leu Val
            340                 345                 350

Glu Glu Val Arg Gly Lys Glu Lys Leu Glu Lys Phe Ser Glu Met Leu
        355                 360                 365

Val Thr Pro Tyr Val Pro Pro Glu
    370                 375
```

<210> SEQ ID NO 7
<211> LENGTH: 1551
<212> TYPE: DNA
<213> ORGANISM: Zea mays

<400> SEQUENCE: 7

```
gcacgagctc ttgtttaggc cgggctcgag agagttgggc tccgaatcct gggtgggttt      60
ggagttggag aatcgccttc gtcgctcgac ccagaaagat tcgatggaga gccacaaccc     120
atcgcactct cagatcgccg aagtgacgat ggacatcgca gcgtcagctt ctggagcggc     180
agggagcaag ttctgcaagg gcgcagcctg cgacttctcc gacgccagca actcctcgaa     240
ggacgccagg gagaggtcgg cgtcgatgag gaagctgata gtcgcggtgg tcctctgcgt     300
cgtattcatg gcggtggagg tggtgggggg catcaaggcg aacagcctgg ccatcctgac     360
cgacgcggcg cacctcctgt cggacgtggc ggcgttcgcc atctcgctgt tctcgctctg     420
ggccgccggg tgggaggcga cgccgcggca gtcgtacggg ttcttccggg tggagatcct     480
cggcgccctc gtctccatcc agctcatctg gctgctcgcc ggcatactgg tgtacgaggc     540
cgtcgtgagg ctcgtcggcg agagcggcga cgtgcggggg tcgctcatgt tcgccgtgtc     600
ggcgttcggg ctggccgtca acgttctcat ggccgtgttg ctgggccatg accacgggca     660
cggccacggc catggacatg gacattcgca tgaccatggc cacggccatg gggattcgga     720
cgatggccat tcccaccacg acgacgagga gcaagaacag gccgtgtcc atcaccacga     780
gcacggccat ggaggcgcta tcactgtcac aacccaccac caccaccatc atcacgatca     840
cgatgttgag gaggcgctga tcaagcatga gggtacccag tctgctggca gagctggtaa     900
gaagcctcgg cggaacatca acgtgcacag cgcatacctc cacgtgctcg gggactccgt     960
ccagagcgtc ggggtcatgg tgggcggggc gatcatctgg tacaagccgg agtggaaggt    1020
catcgacctc atctgcacgc tcgtcttctc ggtggtggtg ctgttcacca cgatccggat    1080
gctgcgcagc atcctcgaag tgttgatgga gagcacgccc cgcgagatcg acgccaccag    1140
gctggagagc gggctctgcg ggatggaggg cgtggtggcc gtccacgagc tgcacatctg    1200
ggccatcacg gtgggcaagg tgctgctggc cgtgccatgt gaccatcgcca gggatgcgga    1260
cgctgatgag atccttgaca aggtgatcgg gtacatcaag acggagtaca acatcagcca    1320
tgtgaccatc caggtcgagc gcgagtaggg agctctgtct ttggctgctg tcttgggcat    1380
aaatggctgg cgccattcga gctctggtgt gctcggtggt gttgtctatt gctagtctat    1440
taggcaggcc gggggaatta tttgcgtggt ggtcgtcagt cagtcagtcg gtgcataaac    1500
aaggatgaaa ttttcggtaa aaaaaaaaaa aaaaaaaaa aaaaaaaaaa a             1551
```

<210> SEQ ID NO 8
<211> LENGTH: 448
<212> TYPE: PRT
<213> ORGANISM: Zea mays

<400> SEQUENCE: 8

```
His Glu Leu Leu Phe Arg Pro Gly Ser Arg Glu Leu Gly Ser Glu Ser
  1               5                  10                  15

Trp Val Gly Leu Glu Leu Glu Asn Arg Leu Arg Arg Ser Thr Gln Lys
             20                  25                  30

Asp Ser Met Glu Ser His Asn Pro Ser His Ser Gln Ile Ala Glu Val
         35                  40                  45

Thr Met Asp Ile Ala Ala Ser Ala Ser Gly Ala Ala Gly Ser Lys Phe
     50                  55                  60
```

```
Cys Lys Gly Ala Ala Cys Asp Phe Ser Asp Ala Ser Asn Ser Ser Lys
 65                  70                  75                  80

Asp Ala Arg Glu Arg Ser Ala Ser Met Arg Lys Leu Ile Val Ala Val
             85                  90                  95

Val Leu Cys Val Val Phe Met Ala Val Glu Val Val Gly Gly Ile Lys
            100                 105                 110

Ala Asn Ser Leu Ala Ile Leu Thr Asp Ala Ala His Leu Leu Ser Asp
        115                 120                 125

Val Ala Ala Phe Ala Ile Ser Leu Phe Ser Leu Trp Ala Ala Gly Trp
130                 135                 140

Glu Ala Thr Pro Arg Gln Ser Tyr Gly Phe Phe Arg Val Glu Ile Leu
145                 150                 155                 160

Gly Ala Leu Val Ser Ile Gln Leu Ile Trp Leu Leu Ala Gly Ile Leu
                165                 170                 175

Val Tyr Glu Ala Val Val Arg Leu Val Gly Ser Gly Asp Val Arg
            180                 185                 190

Gly Ser Leu Met Phe Ala Val Ser Ala Phe Gly Leu Ala Val Asn Val
        195                 200                 205

Leu Met Ala Val Leu Leu Gly His Asp His Gly His Gly His Gly His
210                 215                 220

Gly His Gly His Ser His Asp His Gly His Gly His Gly Asp Ser Asp
225                 230                 235                 240

Asp Gly His Ser His His Asp Asp Glu Glu Gln Glu Gln Gly Arg Val
                245                 250                 255

His His His Glu His Gly His Gly Ala Ile Thr Val Thr Thr His
            260                 265                 270

His His His His His His Asp His Asp Val Glu Glu Ala Leu Ile Lys
        275                 280                 285

His Glu Gly Thr Gln Ser Ala Gly Arg Ala Gly Lys Lys Pro Arg Arg
    290                 295                 300

Asn Ile Asn Val His Ser Ala Tyr Leu His Val Leu Gly Asp Ser Val
305                 310                 315                 320

Gln Ser Val Gly Val Met Val Gly Gly Ala Ile Ile Trp Tyr Lys Pro
                325                 330                 335

Glu Trp Lys Val Ile Asp Leu Ile Cys Thr Leu Val Phe Ser Val Val
            340                 345                 350

Val Leu Phe Thr Thr Ile Arg Met Leu Arg Ser Ile Leu Glu Val Leu
        355                 360                 365

Met Glu Ser Thr Pro Arg Glu Ile Asp Ala Thr Arg Leu Glu Ser Gly
370                 375                 380

Leu Cys Gly Met Glu Gly Val Ala Val His Glu Leu His Ile Trp
385                 390                 395                 400

Ala Ile Thr Val Gly Lys Val Leu Leu Ala Cys His Val Thr Ile Ala
                405                 410                 415

Arg Asp Ala Asp Ala Asp Glu Ile Leu Asp Lys Val Ile Gly Tyr Ile
            420                 425                 430

Lys Thr Glu Tyr Asn Ile Ser His Val Thr Ile Gln Val Glu Arg Glu
        435                 440                 445
```

<210> SEQ ID NO 9
<211> LENGTH: 1873
<212> TYPE: DNA
<213> ORGANISM: Oryza sativa -continued

```
<400> SEQUENCE: 9
gcacgagctt acatgtaagc tcgtgccgaa ttcggcacga gcttacaccc gttctctcct       60
ccccatctcc aacgcacgca cgcgccatca ccaccacctc gacgccggcg gcgacgacca      120
cggcgacggc aacggcggcg gcggcagaga agccctcctc atccccaaga tggacagcca      180
taactcagca cctccccaga ttgctgaagt gagaatggac atctcatcat ctacttctgt      240
agcagctggg aacaaagttt gcagaggtgc tgcttgtgac ttttctgatt ccagtaatag      300
ctcaaaagat gcaagggaga gaatggcgtc aatgaggaag ctcattattg ctgtgatcct      360
ttgcatcata ttcatggcgg tcgaagtggt tggaggtatc aaagcaaaca gtttggcaat      420
cttgactgat gcagcccatc tcctttcgga tgttgcggcc tttgccatat ctttgttctc      480
tctttgggca gctggatggg aagctacacc acagcagtca tatgggtttt tccgtataga      540
aattcttggt gccctggttt ctattcagct catatggctc cttgctggta ttcttgtcta      600
tgaagctatt gtaaggctca ttaatgaaag tggtgaggtc cagggctccc tcatgtttgc      660
tgtctcagca tttggcttat ttgttaacat cataatggct gtcttgcttg gtcatgacca      720
tggacatgga cacggacatg gtcatgggca tggacattcc catgaccatg atcatggtgg      780
ttctgaccat gaccatcacc accatgaaga tcaagagcat ggccatgtac atcaccacga      840
agatggccat ggtaattcaa ttaccgtcaa tctccatcac catccaggca ctggacacca      900
ccaccatgat gctgaggaac cattgctcaa gagtgatgct ggttgtgaca gcacccaatc      960
tggtgccaag gatgccaaga aggctcgtcg taatatcaat gtacacagtg cttatctgca     1020
tgtgcttggg gattcaatcc agagcatcgg tgtgatgatt ggaggggcta tcatctggta     1080
caagcccgag tggaagatta ttgatctcat ctgcaccctc atcttctccg tgatcgtact     1140
cttcaccaca atcaagatgc tgcgcaacat ccttgaggtc ctgatggaga gcacgccccg     1200
cgagatcgat gccaccagcc ttgagaatgg cctccgcgac atggacggtg tggttgcagt     1260
acatgagctg cacatctggg ccataacggt ggggaaggtt ctcctggcgt gccatgtgac     1320
aatcactcag gacgcagacg ctgatcaaat gctggacaag gtgattgggt acatcaagtc     1380
tgagtacaac atcagccatg tgaccattca gattgagcgc gagtaggctt gaccgcttga     1440
gacaggtagg tagtgttgat gatagaacgg atcatcttca tctcatctca tgggaccaac     1500
ttatcaggaa cctgtttcac tggttttatg cagttactgt tagctctgca gtgcaaatca     1560
gatcagcaga gtccaacaat tcctgcaggt tcatctgaat gttagcttct gatgctgttt     1620
attactataa gtacgtgtta ttagtactat cttagtcaat taggtgagtt gatgttaatc     1680
agtttcgtag tcggttgtat tcacatgggt gcagttttca gacaagtttt caggcacctg     1740
tgagtacgtc aacctgcctt ctgcgtctgt agtctagcgc ccagccgtac tagtttttat     1800
gtaaatctgc actggcatgg gaaataataa ccaagtttcg tttggcctta taaaaaaaaa     1860
aaaaaaaaaa aaa                                                        1873

<210> SEQ ID NO 10
<211> LENGTH: 474
<212> TYPE: PRT
<213> ORGANISM: Oryza sativa

<400> SEQUENCE: 10

His Glu Leu Thr Cys Lys Leu Val Pro Asn Ser Ala Arg Ala Tyr Thr
  1               5                  10                  15

Arg Ser Leu Leu Pro Ile Ser Asn Ala Arg Thr Arg His His His
             20                  25                  30
```

-continued

```
Leu Asp Ala Gly Gly Asp Asp His Gly Asp Gly Asn Gly Gly Gly
         35                  40                  45

Arg Glu Ala Leu Leu Ile Pro Lys Met Asp Ser His Asn Ser Ala Pro
         50                  55                  60

Pro Gln Ile Ala Glu Val Arg Met Asp Ile Ser Ser Thr Ser Val
65                  70                  75                  80

Ala Ala Gly Asn Lys Val Cys Arg Gly Ala Ala Cys Asp Phe Ser Asp
                 85                  90                  95

Ser Ser Asn Ser Ser Lys Asp Ala Arg Glu Arg Met Ala Ser Met Arg
                 100                 105                 110

Lys Leu Ile Ile Ala Val Ile Leu Cys Ile Ile Phe Met Ala Val Glu
         115                 120                 125

Val Val Gly Gly Ile Lys Ala Asn Ser Leu Ala Ile Leu Thr Asp Ala
     130                 135                 140

Ala His Leu Leu Ser Asp Val Ala Ala Phe Ala Ile Ser Leu Phe Ser
145                 150                 155                 160

Leu Trp Ala Ala Gly Trp Glu Ala Thr Pro Gln Gln Ser Tyr Gly Phe
                 165                 170                 175

Phe Arg Ile Glu Ile Leu Gly Ala Leu Val Ser Ile Gln Leu Ile Trp
             180                 185                 190

Leu Leu Ala Gly Ile Leu Val Tyr Glu Ala Ile Val Arg Leu Ile Asn
         195                 200                 205

Glu Ser Gly Glu Val Gln Gly Ser Leu Met Phe Ala Val Ser Ala Phe
     210                 215                 220

Gly Leu Phe Val Asn Ile Ile Met Ala Val Leu Leu Gly His Asp His
225                 230                 235                 240

Gly His Gly His Gly His Gly His Gly His Ser His Asp His
                 245                 250                 255

Asp His Gly Gly Ser Asp His Asp His His His Glu Asp Gln Glu
                 260                 265                 270

His Gly His Val His His Glu Asp Gly His Gly Asn Ser Ile Thr
         275                 280                 285

Val Asn Leu His His His Pro Gly Thr Gly His His His Asp Ala
     290                 295                 300

Glu Glu Pro Leu Leu Lys Ser Asp Ala Gly Cys Asp Ser Thr Gln Ser
305                 310                 315                 320

Gly Ala Lys Asp Ala Lys Lys Ala Arg Arg Asn Ile Asn Val His Ser
                 325                 330                 335

Ala Tyr Leu His Val Leu Gly Asp Ser Ile Gln Ser Ile Gly Val Met
             340                 345                 350

Ile Gly Gly Ala Ile Ile Trp Tyr Lys Pro Glu Trp Lys Ile Ile Asp
         355                 360                 365

Leu Ile Cys Thr Leu Ile Phe Ser Val Ile Val Leu Phe Thr Thr Ile
     370                 375                 380

Lys Met Leu Arg Asn Ile Leu Glu Val Leu Met Glu Ser Thr Pro Arg
385                 390                 395                 400

Glu Ile Asp Ala Thr Ser Leu Glu Asn Gly Leu Arg Asp Met Asp Gly
                 405                 410                 415

Val Val Ala Val His Glu Leu His Ile Trp Ala Ile Thr Val Gly Lys
             420                 425                 430

Val Leu Leu Ala Cys His Val Thr Ile Thr Gln Asp Ala Asp Ala Asp
         435                 440                 445
```

```
Gln Met Leu Asp Lys Val Ile Gly Tyr Ile Lys Ser Glu Tyr Asn Ile
    450                 455                 460

Ser His Val Thr Ile Gln Ile Glu Arg Glu
465                 470

<210> SEQ ID NO 11
<211> LENGTH: 1208
<212> TYPE: DNA
<213> ORGANISM: Glycine max

<400> SEQUENCE: 11
ttcggcacga gcatgactgt tgaagtggtt ggtggcatca aagctaacag tcttgctata      60
ttgactgatg cagctcattt gctttcagat gttgcatcct ttgccatctc cttattttca     120
ttatgggctg ctggatggga agctacacct cgccagtcat atggattttt ccgaatagag     180
attcttggtg ctttggtttc tattcaaatg atatggttgc ttgctgggat tctggtatat     240
gaagccattg atagaatcat tgctggtcct aaaaatgtgg atggtttttt aatgttttta     300
gtttctgcat ttggtcttgt ggttaatatc atcatggcat tgttattggg tcatgatcat     360
ggccacagac atgctggtca cagtcacgga cacggacatg atggtcatgg ccacagtcat     420
ggatttacaa tgtctaccca ttgtgatgca aagcatacca aagatcagca ccatcacaca     480
caccatcatg atgaaaacca tccaaaagat gctcaccatc atactgatga agatcacttg     540
caccatcatg ctcacaaaga ggttactgaa ctgcttcttg gtgagtcaaa aggtggaact     600
aagaagaaga agcaatggaa cataaatgta caggggcttt atctccatgt tcttggggac     660
tctatccaaa gtattggggt aatgattggg ggagcagtca tatggtataa ccctcgttgg     720
caaattgttg atttaatctg cactctaatc ttttcagtaa ttgttatggg gacaaccatc     780
aacatgctgc gaaacatttt ggaagtcctg atggagaaca cacctcgtga gatagatgct     840
actaagcttg aaagggggct gttggatatg aagatgtag tggccgttca tgaactgcat      900
atatgggcca ttacagtggg aaaggttttg cttgcatgtc atgttaagat cagacgtgaa     960
gcagatgcag acttggtgct ggacaaggtt atagactata tcaaaagggt ttataacatc    1020
agccatgtca ccatacagat agagcgttag aattttcctt ctttaattga ctattttctg    1080
gtagtaaaga ttagagggga aggatttagt tggacttgag gaattgttct ggaactcaaa    1140
tttgtcgatg ttcttatatt cttctatcta gaagtttaag agtgcagatt aaaaaaaaaa    1200
aaaaaaaa                                                             1208

<210> SEQ ID NO 12
<211> LENGTH: 349
<212> TYPE: PRT
<213> ORGANISM: Glycine max

<400> SEQUENCE: 12

Phe Gly Thr Ser Met Thr Val Glu Val Val Gly Gly Ile Lys Ala Asn
 1               5                  10                  15

Ser Leu Ala Ile Leu Thr Asp Ala Ala His Leu Leu Ser Asp Val Ala
             20                  25                  30

Ser Phe Ala Ile Ser Leu Phe Ser Leu Trp Ala Ala Gly Trp Glu Ala
         35                  40                  45

Thr Pro Arg Gln Ser Tyr Gly Phe Phe Arg Ile Glu Ile Leu Gly Ala
     50                  55                  60

Leu Val Ser Ile Gln Met Ile Trp Leu Leu Ala Gly Ile Leu Val Tyr
 65                  70                  75                  80
```

```
Glu Ala Ile Asp Arg Ile Ile Ala Gly Pro Lys Asn Val Asp Gly Phe
                85                  90                  95
Leu Met Phe Leu Val Ser Ala Phe Gly Leu Val Val Asn Ile Ile Met
            100                 105                 110
Ala Leu Leu Leu Gly His Asp His Gly His Arg His Ala Gly His Ser
        115                 120                 125
His Gly His Gly His Asp Gly His Gly Ser His Gly Phe Thr Met
    130                 135                 140
Ser Thr His Cys Asp Ala Lys His Thr Lys Asp Gln His His His Thr
145                 150                 155                 160
His His His Asp Glu Asn His Pro Lys Asp Ala His His Thr Asp
                165                 170                 175
Glu Asp His Leu His His His Ala His Lys Glu Val Thr Glu Leu Leu
            180                 185                 190
Leu Gly Glu Ser Lys Gly Gly Thr Lys Lys Lys Gln Trp Asn Ile
        195                 200                 205
Asn Val Gln Gly Ala Tyr Leu His Val Leu Gly Asp Ser Ile Gln Ser
    210                 215                 220
Ile Gly Val Met Ile Gly Gly Ala Val Ile Trp Tyr Asn Pro Arg Trp
225                 230                 235                 240
Gln Ile Val Asp Leu Ile Cys Thr Leu Ile Phe Ser Val Ile Val Met
                245                 250                 255
Gly Thr Thr Ile Asn Met Leu Arg Asn Ile Leu Glu Val Leu Met Glu
            260                 265                 270
Asn Thr Pro Arg Glu Ile Asp Ala Thr Lys Leu Glu Arg Gly Leu Leu
        275                 280                 285
Asp Met Glu Asp Val Val Ala Val His Glu Leu His Ile Trp Ala Ile
    290                 295                 300
Thr Val Gly Lys Val Leu Leu Ala Cys His Val Lys Ile Arg Arg Glu
305                 310                 315                 320
Ala Asp Ala Asp Leu Val Leu Asp Lys Val Ile Asp Tyr Ile Lys Arg
                325                 330                 335
Val Tyr Asn Ile Ser His Val Thr Ile Gln Ile Glu Arg
            340                 345
```

<210> SEQ ID NO 13
<211> LENGTH: 790
<212> TYPE: DNA
<213> ORGANISM: Triticum aestivum

<400> SEQUENCE: 13

```
gcacgaggtc tggagccaag cctgccaaga agcctcgccg taacatcaat gttcacagtg    60
cctatctgca tgtaattggg gactccatcc agagcatcgg tgtaatgatt ggagggctc    120
tcatctggta caagcccgaa tggaagatta ttgatctcat atgcaccctc atcttctctg    180
tgattgtact gttcaccaca atcaggatga ttcggaacat actggaagtt cttatggaga    240
gcacgccccg tgagatcgat gccaccaggc ttgagagtgg tctccgtgag atggaaggtg    300
tgattgcggt ccatgagctg cacatctggg ctatcacagt ggggaaggtg ctcttggcat    360
gccatgtgac gatcacgcag gatgcggatg ctgataaaat gcttgacaag gtcattgggt    420
acatcaaggc agagtacaac atcagtcatg tgaccattca gattgagcga gagtaaggca    480
catgtcaggt agttgaggat aaaggtgtgc ctgttagtgg ttgatcatct taaaatgcgg    540
ttaatgttag atttgcactt gcaaaggcgt tgcaggttca tctagctgtt gcctctggtg    600
```

-continued

```
ctggagaaat attatatgta tgcgtttcca ttagcccatt agttaaatga actattaaac    660
gggtggtgta gtcgtttata ttcacatgga tgcaattttc agacagtttt tgagccttgt    720
gagtttatca acctgcacgt gtagtttcag cggcaaaaaa aaaaaaaaaa aaaaaaaaaa    780
aaaaaaaaaa                                                           790
```

<210> SEQ ID NO 14
<211> LENGTH: 157
<212> TYPE: PRT
<213> ORGANISM: Triticum aestivum

<400> SEQUENCE: 14

```
Thr Arg Ser Gly Ala Lys Pro Ala Lys Lys Pro Arg Arg Asn Ile Asn
  1               5                  10                  15

Val His Ser Ala Tyr Leu His Val Ile Gly Asp Ser Ile Gln Ser Ile
                 20                  25                  30

Gly Val Met Ile Gly Gly Ala Leu Ile Trp Tyr Lys Pro Glu Trp Lys
             35                  40                  45

Ile Ile Asp Leu Ile Cys Thr Leu Ile Phe Ser Val Ile Val Leu Phe
         50                  55                  60

Thr Thr Ile Arg Met Ile Arg Asn Ile Leu Glu Val Leu Met Glu Ser
 65                  70                  75                  80

Thr Pro Arg Glu Ile Asp Ala Thr Arg Leu Glu Ser Gly Leu Arg Glu
                 85                  90                  95

Met Glu Gly Val Ile Ala Val His Glu Leu His Ile Trp Ala Ile Thr
            100                 105                 110

Val Gly Lys Val Leu Leu Ala Cys His Val Thr Ile Thr Gln Asp Ala
        115                 120                 125

Asp Ala Asp Lys Met Leu Asp Lys Val Ile Gly Tyr Ile Lys Ala Glu
    130                 135                 140

Tyr Asn Ile Ser His Val Thr Ile Gln Ile Glu Arg Glu
145                 150                 155
```

<210> SEQ ID NO 15
<211> LENGTH: 332
<212> TYPE: PRT
<213> ORGANISM: Homo sapiens

<400> SEQUENCE: 15

```
Met Leu Leu Asp Val Glu Pro Leu Glu Pro Thr Leu Ser Asn Ile Ile
  1               5                  10                  15

Glu Gln Arg Ser Leu Lys Trp Ile Phe Val Gly Gly Lys Gly Gly Val
                 20                  25                  30

Gly Lys Thr Thr Cys Ser Cys Ser Leu Ala Val Gln Leu Ser Lys Gly
             35                  40                  45

Arg Glu Ser Val Leu Ile Ile Ser Thr Asp Pro Ala His Asn Ile Ser
         50                  55                  60

Asp Ala Phe Asp Gln Lys Phe Ser Lys Val Pro Thr Lys Val Lys Gly
 65                  70                  75                  80

Tyr Asp Asn Leu Phe Ala Met Glu Ile Asp Pro Ser Leu Gly Val Ala
                 85                  90                  95

Asp Val Pro Asp Glu Phe Phe Glu Glu Asp Asn Met Leu Ser Met Gly
            100                 105                 110

Lys Lys Met Met Gln Glu Ala Met Ser Ala Phe Pro Gly Ile Asp Glu
        115                 120                 125

Ala Met Ser Tyr Ala Glu Val Met Arg Leu Val Lys Gly Met Asn Phe
```

-continued

```
            130                 135                 140
Ser Val Val Phe Asp Thr Ala Pro Thr Gly His Thr Leu Arg Leu
145                 150                 155                 160

Leu Asn Phe Pro Thr Ile Val Glu Arg Gly Leu Gly Arg Leu Met Gln
                    165                 170                 175

Ile Lys Asn Gln Ile Ser Pro Phe Ile Ser Gln Met Cys Asn Met Leu
                180                 185                 190

Gly Leu Gly Asp Met Asn Ala Asp Gln Leu Ala Ser Lys Leu Glu Glu
                195                 200                 205

Thr Leu Pro Val Ile Arg Ser Val Ser Glu Gln Phe Lys Asp Pro Glu
                210                 215                 220

Gln Thr Thr Phe Ile Cys Val Cys Ile Ala Glu Phe Leu Ser Leu Tyr
225                 230                 235                 240

Glu Thr Glu Arg Leu Ile Gln Glu Leu Ala Lys Cys Lys Ile Asp Thr
                    245                 250                 255

His Asn Ile Ile Val Asn Gln Leu Val Phe Pro Asp Pro Glu Lys Pro
                260                 265                 270

Cys Lys Met Cys Glu Ala Arg His Lys Ile Gln Ala Lys Tyr Leu Asp
                275                 280                 285

Gln Met Glu Asp Leu Tyr Glu Asp Phe His Ile Val Lys Leu Pro Leu
                290                 295                 300

Leu Pro His Glu Val Arg Gly Ala Asp Lys Val Asn Thr Phe Ser Ala
305                 310                 315                 320

Leu Leu Leu Glu Pro Tyr Lys Pro Pro Ser Ala Gln
                325                 330

<210> SEQ ID NO 16
<211> LENGTH: 342
<212> TYPE: PRT
<213> ORGANISM: Caenorhabditis elegans

<400> SEQUENCE: 16

Met Ser Asp Gln Leu Glu Ala Ser Ile Lys Asn Ile Leu Glu Gln Lys
1               5                   10                  15

Thr Leu Lys Trp Ile Phe Val Gly Gly Lys Gly Gly Val Gly Lys Thr
                20                  25                  30

Thr Cys Ser Cys Ser Leu Ala Ala Gln Leu Ser Lys Val Arg Glu Arg
            35                  40                  45

Val Leu Leu Ile Ser Thr Asp Pro Ala His Asn Ile Ser Asp Ala Phe
        50                  55                  60

Ser Gln Lys Phe Thr Lys Thr Pro Thr Leu Val Glu Gly Phe Lys Asn
65              70                  75                  80

Leu Phe Ala Met Glu Ile Asp Ser Asn Pro Asn Gly Glu Gly Val Glu
                85                  90                  95

Met Gly Asn Ile Glu Glu Met Leu Gln Asn Ala Ala Gln Asn Glu Gly
                100                 105                 110

Gly Ser Gly Gly Phe Ser Met Gly Lys Asp Phe Leu Gln Ser Phe Ala
            115                 120                 125

Gly Gly Leu Pro Gly Ile Asp Glu Ala Met Ser Phe Gly Glu Met Ile
        130                 135                 140

Lys Leu Ile Asp Ser Leu Asp Phe Asp Val Val Phe Asp Thr Ala
145                 150                 155                 160

Pro Thr Gly His Thr Leu Arg Leu Leu Gln Phe Pro Thr Leu Leu Glu
                165                 170                 175
```

```
Lys Val Phe Thr Lys Ile Leu Ser Leu Gln Gly Met Phe Gly Pro Met
            180                 185                 190

Met Asn Gln Phe Gly Gly Met Phe Gly Met Gly Gly Ser Met Asn
        195                 200                 205

Glu Met Ile Glu Lys Met Thr Thr Leu Glu Ser Val Lys Lys Met
210             215                 220

Asn Ala Gln Phe Lys Asp Pro Asn Cys Thr Thr Phe Val Cys Val Cys
225             230                 235                 240

Ile Ala Glu Phe Leu Ser Leu Tyr Glu Thr Glu Arg Leu Ile Gln Glu
                245                 250                 255

Leu Ser Lys Gln Gly Ile Asp Thr His Asn Ile Ile Val Asn Gln Leu
            260                 265                 270

Leu Phe Pro Asp Thr Asp Ala Asn Gly Thr Val Ser Cys Arg Lys Cys
        275                 280                 285

Ala Ser Arg Gln Ala Ile Gln Ser Lys Tyr Leu Thr Asp Ile Asp Glu
    290                 295                 300

Leu Tyr Glu Asp Phe His Val Val Lys Leu Pro Leu Leu Glu Ala Glu
305             310                 315                 320

Val Arg Gly Gly Pro Ala Ile Leu Gln Phe Ser Glu Arg Met Val Asp
                325                 330                 335

Pro Glu Ala Asn Lys Asn
            340

<210> SEQ ID NO 17
<211> LENGTH: 398
<212> TYPE: PRT
<213> ORGANISM: Arabidopsis thaliana

<400> SEQUENCE: 17

Met Glu Ser Ser Ser Pro His His Ser His Ile Val Glu Val Asn Val
1               5                   10                  15

Gly Lys Ser Asp Glu Glu Arg Ile Ile Val Ala Ser Lys Val Cys Gly
            20                  25                  30

Glu Ala Pro Cys Gly Phe Ser Asp Ser Lys Asn Ala Ser Gly Asp Ala
        35                  40                  45

His Glu Arg Ser Ala Ser Met Arg Lys Leu Cys Ile Ala Val Val Leu
    50                  55                  60

Cys Leu Val Phe Met Ser Val Glu Val Gly Gly Ile Lys Ala Asn
65              70                  75                  80

Ser Leu Ala Ile Leu Thr Asp Ala Ala His Leu Leu Ser Asp Val Ala
                85                  90                  95

Ala Phe Ala Ile Ser Leu Phe Ser Leu Trp Ala Ala Gly Trp Glu Ala
            100                 105                 110

Thr Pro Arg Gln Thr Tyr Gly Phe Phe Arg Ile Glu Ile Leu Gly Ala
        115                 120                 125

Leu Val Ser Ile Gln Leu Ile Trp Leu Leu Thr Gly Ile Leu Val Tyr
    130                 135                 140

Glu Ala Ile Ile Arg Ile Val Thr Glu Thr Ser Glu Val Asn Gly Phe
145             150                 155                 160

Leu Met Phe Leu Val Ala Ala Phe Gly Leu Val Val Asn Ile Ile Met
                165                 170                 175

Ala Val Leu Leu Gly His Asp His Gly His Ser His Gly His Gly His
            180                 185                 190

Gly His Gly His Asp His His Asn His Ser His Gly Val Thr Val Thr
        195                 200                 205
```

```
Thr His His His His Asp His Glu His Gly His Ser His Gly His
    210             215             220

Gly Glu Asp Lys His His Ala His Gly Asp Val Thr Glu Gln Leu Leu
225             230             235                         240

Asp Lys Ser Lys Thr Gln Val Ala Ala Lys Glu Lys Arg Lys Arg Asn
            245             250             255

Ile Asn Leu Gln Gly Ala Tyr Leu His Val Leu Gly Asp Ser Ile Gln
            260             265             270

Ser Val Gly Val Met Ile Gly Gly Ala Ile Ile Trp Tyr Asn Pro Glu
        275             280             285

Trp Lys Ile Val Asp Leu Ile Cys Thr Leu Ala Phe Ser Val Ile Val
    290             295             300

Leu Gly Thr Thr Ile Asn Met Ile Arg Asn Ile Leu Glu Val Leu Met
305             310             315                         320

Glu Ser Thr Pro Arg Glu Ile Asp Ala Thr Lys Leu Glu Lys Gly Leu
            325             330             335

Leu Glu Met Glu Glu Val Val Ala Val His Glu Leu His Ile Trp Ala
            340             345             350

Ile Thr Val Gly Lys Val Leu Leu Ala Cys His Val Asn Ile Arg Pro
        355             360             365

Glu Ala Asp Ala Asp Met Val Leu Asn Lys Val Ile Asp Tyr Ile Arg
    370             375             380

Arg Glu Tyr Asn Ile Ser His Val Thr Ile Gln Ile Glu Arg
385             390             395
```